United States Patent [19]
Hölderich et al.

[11] Patent Number: 5,968,242
[45] Date of Patent: Oct. 19, 1999

[54] COLOURANT-LOADED MOLECULAR SIEVE

[75] Inventors: Wolfgang Hölderich, Frankenthal; Nadja Röhrlich, Aachen, both of Germany; Laurent Chassot, Praroman, Switzerland

[73] Assignee: Ciba Specialty Chemicals Corporation, Tarrytown, N.Y.

[21] Appl. No.: 08/994,218

[22] Filed: Dec. 19, 1997

[30] Foreign Application Priority Data

Dec. 19, 1996 [CH] Switzerland ............... 3123/96

[51] Int. Cl.⁶ .................................. C09D 11/12
[52] U.S. Cl. ................ 106/31.6; 106/400; 106/401; 106/402; 106/467; 106/483; 106/493; 106/496; 106/497; 106/498; 423/700; 423/704; 423/705; 423/706; 424/70.1; 424/70.11; 424/78.03; 501/1; 501/32; 502/1; 502/62; 502/150; 502/162; 502/167; 523/200

[58] Field of Search ................... 106/493, 496, 106/497, 498, 400, 401, 402, 467, 483, 31.6; 423/700, 704, 705, 706; 502/1, 62, 150, 162, 167; 523/200; 424/78.03, 70.6, 70.1, 70.11; 501/32, 1

*Primary Examiner*—Mark L. Bell
*Assistant Examiner*—Scott L. Hertzog
*Attorney, Agent, or Firm*—Kevin T. Mansfield; David R. Crichton

[57] ABSTRACT

A molecular sieve, which contains in all, or only in some, of its cavities colorant molecules as well as a modifier which is covalently bound to said molecular sieve and which reduces its pore diameter, a process for its preparation as well as its use as pigment for coloring high molecular weight organic materials, preferably biopolymers and plastic materials, glasses, ceramic products, for formulations of decorative cosmetics, for the preparation of paint systems, preferably automotive lacquers, printing inks, dispersion paints and color filters as well as materials comprising the novel molecular sieves.

10 Claims, No Drawings

COLOURANT-LOADED MOLECULAR SIEVE

The present invention relates to a molecular sieve, containing in all, or only in some, of its cavities colorant molecules as well as a modifier which is covalently bound to said molecular sieve and which reduces its pore diameter.

This invention also relates to a process for the preparation of the novel molecular sieve as well as to the use thereof as pigment for coloring high molecular weight organic materials, preferably biopolymers and plastic materials, glasses, ceramic products, for formulations of decorative cosmetics, for the preparation of paint systems, preferably automotive lacquers, printing inks, dispersion paints and color filters as well as to materials comprising the novel molecular sieves.

Dyes adsorbed to molecular sieves have been known for some time (see DE-A 41 26 461, p.2, lines 5–21). The interaction between the dyes and the molecular sieves is usually so strong that desorption is only rarely found when the dye is heated. In suitable solvents, on the other hand, desorption may occur, adsorbed dye molecules being removed by leaching.

U.S. Pat. No. 4,018,870 describes the synthesis of silicon-containing molecular sieves in the presence of methylene blue and acriflavine as templates, both of which are water-soluble basic dyes. In this so-called template synthesis, the molecular sieve is synthesised in the presence of a compound serving as molecular template. The templates, in the present case the dye molecules, are thus inserted into the forming cavities of the corresponding molecular sieve. By this principle, specific molecular sieves are accessible, depending on the template. To obtain molecular sieves having free pores and cavities, the organic template compounds retained in the cavities of the molecular sieves so obtained are driven off by heating.

To overcome the drawback of leaching, DE-A 41 26 461 proposes, in accordance with the cited U.S. document, to insert dye molecules into the framework of the molecular sieve. DE-A 41 26 461 describes, in particular, dye-loaded inorganic molecular sieves, a water-insoluble organic dye being irreversibly inserted into the cavity framework of the molecular sieve. The molecular sieves disclosed in DE-A 41 26 461 are accessible by template synthesis. The preconditions for the irreversible insertion of the dye molecules are dye molecule sizes of at most the size of the cavities of the molecular sieve and larger than its free pore diameter.

Zeolites 4 (1984), p. 30–34, gives a description of the so-called ship-in-the-bottle synthesis of cobalt phthalocyanines, nickel phthalocyanines and copper phthalocyanines (Pc) in the faujasite zeolite. In this method, the cations present in the zeolite are first exchanged for the cited transition metal cations. In a subsequent step, the corresponding Pc complex is then formed inter alia in the cavities of the faujasite by the addition of ortho-phthalodinitrile. The Pc complexes formed in the cavities normally do not diffuse from the cavities for sterical reasons. However, in some applications this happens unwantedly.

The molecular sieves described in DE-A 41 26 461, U.S. Pat. No. 4,018,870 and in Zeolites 4 (1984) have the disadvantage that the number of possible dye-molecular sieve combinations in which dye molecules are, or should be, irreversibly retained in the molecular sieve, is limited by the size of the dye molecules in conjunction with the cavity volume and free pore diameters. Moreover, in the case of DE-A 41 26 461, amines, such as triethanolamine, must be added as templates. However, the templates remain partly in the molecular sieves, preventing the molecular sieve from being completely loaded with the dye. Finally, dyes such as thioindigo are also mentioned which, owing to their molecule size, can diffuse from the pores of the molecular sieves.

The loading of the surface of the molecular sieves, in particular of the pore diameter, has been repeatedly described in the literature:

In "Acid-Base Catalysis", Proceedings of the International Symposium on Acid Base Catalysis Sapporo, (Nov. 28–Dec. 1, 1988), VCH and Kodansha, edited by Tanabe, Hattori, Yamaguchi and Tanaca, p. 255–266, Muracami et al. describe the influence of the pore size on the shape selectivity in crack reactions. According to the method described by Muracami et al., the pore size changes when the zeolites are treated with silicone alkoxides.

In Catalysis Letters 22 (1993), p.107–121, Ribeiro describes the change of the pore diameter of zeolites with metal chlorides, such as $SiCl_4$, $ZnCl_2$, $GaCl_3$, $GeCl_4$, $TiCl_4$, $SnCl_4$ and $Si(OMe)_4$, silane $(SiH_4)$, disilane $(Si_2H_6)$, and diborane $(B_2H_6)$. He discusses, in particular, the influence that the degree of surface loading has with respect to the yield of para-xylene when toluene is alkylated with methanol.

Vansant et al. describe detailed research on the change of the pore diameter in zeolites using silane and diborane (J.Chem.Soc., Faraday Trans. 1, 1983,79, 2821–2834) and disilane (J.Phys.Chem. 1990, 94, 2582–2586).

In Microporous Materials, 2 (1994) p. 251–259, Benazzi et al. describe the pore narrowing in zeolites by treatment with different tetraalkyltin compounds ($SnR_4$ (R=Me, Et, i-Pr, Ph and cyclohexyl) and $Bu_3SnH$.

WO 92/21726 discloses pigments with combined structure, wherein at least one layer of a water-soluble colorant is adsorbed on a water-insoluble core material, the colorant in turn being coated with a transparent layer. Transparent layers mentioned are materials consisting of aluminium oxide, aluminium silicate and amorphous silicic acid, which latter is obtainable from sodium silicate or silica sol. The drawback of this method is, on the one hand, that it is restricted to only water-soluble colorants and, on the other hand, that the adhesion of the colorant by adsorption is insufficient for many applications, in particular in case of thermal or mechanical stress.

Accordingly, it is the object of this invention to provide colorant-loaded molecular sieves which do not have the above disadvantages. To be improved are, in particular, leaching, bleeding, i.e. the migration of the colorants in plastic materials into another material in contact with the plastic material, thermal stability, resistance to solvents, light stability and chemical resistance, and the colorant load of the molecular sieve should be increased.

In accordance with the above, the molecular sieve defined at the outset was found, which contains in all, or only in some of its cavities, colorant molecules as well as a modifier which is covalently bound to said molecular sieve and which reduces its pore diameter.

Furthermore, there was found a process for its preparation as well as its use as pigment for coloring high molecular weight organic materials, preferably biopolymers and plastic materials, glasses, ceramic products, for formulations of decorative cosmetics, for the preparation of paint systems, preferably automotive lacquers, printing inks, inks, dispersion paints and color filters, and also the materials comprising the novel molecular sieve.

The novel molecular sieve contains in all, or only in some of its cavities, colorant molecules.

In addition, the novel molecular sieve comprises a modifier which is covalently bound to it and which reduces its pore diameter. Findings so far have shown that the modifier preferably reacts with the functional groups, such as OH groups, of the molecular sieve which are present on its external surface. This also results in a reduction of the pore diameter which may be indirectly determined by the fact that it is possible to prepare modified molecular sieves which do not leach and/or bleed. This can be explained by the fact that the colorant molecules present in the cavities of a molecular sieve thus modified cannot pass through the now narrowed pores and are therefore retained in the cavities.

It is also possible to carry out the modification such that, for example, not all pores are narrowed, in particular by controlling the amount of modifier and the reaction time with the modifier. Molecular sieves prepared in this manner can still bleed or leach but do so to a lesser extent than unmodified molecular sieves. Depending on the desired application, it is therefore possible to carry out the modification such that molecular sieves are obtained which bleed and/or leach more or less or which do not bleed and/or leach anymore at all. It goes without saying that molecular sieves having micropores usually require a smaller amount of modifier than mesoporous molecular sieves.

The novel molecular sieves are obtainable (a) by completely or partially filling their cavities with colorant molecules and subsequently reducing their pore diameter by reaction with a modifier, or (b) by reducing the pore diameter of a molecular sieve filled in all, or only in some, of its cavities with colorant molecules by reaction with a modifier.

According to findings so far, modifiers may be all those known compounds or the mixtures thereof which are able to form covalent bonds with the functional groups of the molecular sieve which are present on the external surface of molecular sieves, including the externally oriented pore openings, in particular those compounds which are able to reduce the pore diameters of molecular sieves.

The modifier used is preferably at least one compound selected from the group consisting of metal halides, silicon alkoxides, carbon/tin compounds, silicon hydride compounds, tetraalkylorthosilicates, trialkyl-, dialkyl-, monoalkyl- and triarylchlorosilanes, disiloxanes, diborane, silicate sols and silicate colloids as well as halogenated polysiloxanes.

Metal halides, preferably metal chlorides, may be $SiCl_4$, $ZnCl_2$, $GaCl_3$, $GeCl_4$, $TiCl_4$, $SnCl_4$, as described by Ribeiro in Catalysis Letters 22 (1993), p.107–121. Silicium tetrachloride is particularly preferred.

Silicon alkoxides may preferably be silicon tetraalkoxides, such as $Si(OR)_4$ (with R=Me, Et, n-, i-Pr, n-, i-, sec- and tert-Bu), particularly preferably $Si(OMe)_4$, as described by Muracami et al. (see above).

Suitable carbon/tin compounds are, in particular, tetraalkyltin compounds, for example $SnR_4$ (R=Me, Et, i-Pr) and also $SnPh_4$ and $Sn(cyclohexyl)_4$ and $Bu_3SnH$ (described, inter alia, by Benazzi et al. (see above).

Suitable silicon hydrides compounds are preferably silane and disilane (see Vansant et al., mentioned above).

Tetraalkylorthosilicates may preferably be $C_1$–$C_4$tetraorthosilicates, in particular tetraethylorthosilicate (TEOS).

It is also possible to use tri-, di- and monoalkyl- and triarylchlorosilanes, for example $ClSiR_3$ with R=methyl, ethyl, n-, i-Pr, n-, i-, sec- and tert-Bu, phenyl, particularly preferably trimethylchlorosilane and triethylchlorosilane, disiloxanes, typically hexa($C_1$–$C_4$alkyl)disiloxanes, preferably hexamethyidisiloxane, diborane and alkali metal silicates, for example sodium silicate and silica sol (which latter is commercially available under the registered trade mark LUDOX®, of DuPont).

In another of its embodiments, this invention relates to a process for the preparation of the novel molecular sieves by (a) completely or partially filling the cavities of a molecular sieve with colorant molecules and then narrowing its pore diameter by reaction with a modifier, or (b) by narrowing the pore diameters of a molecular sieve which is filled in all, or only in some, of its cavities with colorant molecules by reaction with a modifier.

The amount of modifier to be used usually depends on the desired objective, i.e. to what degree e.g. bleeding or leaching should be prevented. An effective amount of modifier is therefore normally used which may, if necessary, be determined by preliminary tests.

In a preferred embodiment of this invention, silicon-containing modifiers are used, such as those mentioned above, and their amount is chosen, for example, such, that the silicon content of the colorant-containing molecular sieve is increased to the range of 3 to 60% by weight, preferably of 10 to 50% by weight, particularly preferably of 20 to 40% by weight, based on the colorant-containing molecular sieve.

The temperature during the reaction with the modifier generally depends on the type of modifier, on the desired speed at which the modifier is to be applied, as well as on the desired layer thickness. The upper limit of the temperature range is normally determined by the heat stability of the colorant. The corresponding temperature ranges are known from the literature (see above) and may, if required, easily be determined by the skilled person by corresponding preliminary tests. For instance, when using silicon tetrachloride, the temperature is chosen from the range of 20 to 300° C., preferably of 100 to 200° C., and when using TEOS, the temperature is chosen from the range of 20 to 400, preferably of 20 to 250, particularly preferably of 50 to 150° C.

The pressure used during the reaction with the modifier normally depends on the type of modifier, the desired speed at which the modifier is to be applied, the desired layer thickness as well as on the method of application, i.e. in the vapour phase or liquid phase.

When reacting the modifier in the liquid phase, the modifier is usually contacted with the colorant-loaded molecular sieve over a period of time in the range from 0.5h to 3 days, preferably from 0.5 to 2 days, for example by bringing the components together, if desired in the presence of a solvent, and then stirring them.

Depending on the type of modifier, it is possible, if desired, to follow the above treatment by a hydrolysis step, which procedure is preferred in the case of modifiers which react with the molecular sieve only in the presence of water, especially if the amount of water present in the molecular sieve or in the liquid phase is not sufficient for the entire reaction.

If the vapour phase is chosen as reaction medium, then the modifier is normally passed over the colorant-loaded molecular sieve using a customary inert gas, for example nitrogen, and noble gases, such as helium, neon and argon, as carriers. If desired, it is also possible to follow this vapour gas method by a hydrolysis step as described above.

If desired, the molecular sieve can be dried before and/or after applying the modifier, i.e. the water may be driven off to a desired degree in per se customary manner.

In a particularly preferred embodiment of this invention, the reaction is carried out using the modifier silicon tetrachloride by passing an inert gas stream, the preferred inert gas being nitrogen, through the silicon tetrachloride which has a temperature in the range from −10 to 120, preferably from 0 to 60, particularly preferably from 15 to 40° C. The inert gas stream saturated in this manner is then passed over a sample of the colorant-loaded molecular sieve which has been heated to a temperature in the range from 20 to 300, preferably from 120 to 180° C. The pressure is usually chosen from the range of typically 10 to 300, preferably of 90 to 110 kPa. The reaction time is normally chosen from the range of 5 min to 10 h, preferably of 30 min to 5 h, particularly preferably of 1 to 3 h. The amount of the gas stream is usually chosen from the range of 0.25 to 7.5, preferably of 0.5 to 2.5, particularly preferably from 0.75 to 2 l/h, per g of colorant-loaded molecular sieve.

In another preferred embodiment of this invention, a colorant-loaded molecular sieve is used which has a water content of more than zero, the preferred water content being sufficiently high as to accelerate the reaction of the modifier with the functional groups of the molecular sieve, e.g. the OH groups.

According to findings to far, the success of this invention does not rely on the choice of the colorant and of the molecular sieve.

Colorant-loaded molecular sieves are generally accessible by three preparation methods:

(a) by treating a mixture consisting of a usually calcined molecular sieve and a colorant, normally at elevated temperatures. The usual precondition is that the colorant molecules and pore system of the molecular sieves are sterically and electronically compatible.

In a particularly preferred embodiment of this invention, readily sublimable colorants are used, in particular dyes. It is recommended to carry out this treatment under vacuum. In this method, a mixture consisting of dye and molecular sieve is heated to a temperature in the range of 50 to 300° C., preferably of 100 to 250° C., at a pressure of less than 100 kPa (1 bar), preferably of not more than 5 kPa (50 mbar), particularly preferably of not more than 1 kPa (10 mbar) and, very particularly preferably, of not more than 0.1 kPa (1 mbar). The temperature is usually kept in this range for 0.5 to 5 days, preferably for 1 to 4 days, more preferably for 2.5 to 3.5 days. After this treatment, excess dye, i.e. dye which is not bound in the molecular sieve, can be removed by suitable treatment, for example by extraction, in particular by Soxhlet extraction.

(b) by synthesising colorants in the presence of molecular sieves (ship-in-the-bottle synthesis). The principle of this method has been described in detail, inter alia, in Zeolites 4 (1984) p.30, so that further explanations may be dispensed with here. According to this method, the size of the educt molecules is preferably chosen such that they fit into the cavities of the molecular sieves. Subsequent to the synthesis of the colorant in the cavities of the molecular sieve, excess educt and colorants, in particular dyes, formed outside of the cavities are removed by suitable treatment, typically by washing with a solvent.

(c) by synthesising the molecular sieve in the presence of the colorant (template synthesis). The template synthesis of molecular sieves has been described in detail, inter alia, in U.S. Pat. No. 4,018,870 and DE-A 41 26 461, so that further explanations may be dispensed with here. The template synthesis is usually carried out by adding the colorant, in particular dyes, i.e. soluble compounds, and usually, depending on the colorant, another template, to a conventional molecular sieve synthesis mixture which consists, for example, of a silicon source and, if required, of an aluminium source. This mixture is normally subjected to hydrothermal treatment in an autoclave at a temperature in the range from 100 to 250° C. After this treatment, unreacted educts, in particular the colorant, may be removed from the molecular sieve in a manner known per se, for example by washing or extracting with suitable solvents or sieves.

If desired, the molecular sieves may be dehydrated prior to loading them with the colorant at elevated temperature and/or at reduced pressure.

The insertion of the colorant molecules into the molecular sieve may be confirmed by X-ray powder diffraction analysis and via the determination of the adsorption capacity of e.g. nitrogen. The X-ray powder diffractograms (measured at 120° C.) of colorant-loaded molecular sieves and of those not containing any colorant are normally very similar, but they usually differ in the exact position of the diffraction lines and in the intensities of the individual lines. A comparison of nitrogen adsorption isotherms of colorant-loaded molecular sieves of this invention with those of molecular sieves not containing any colorants, or of those which are only partially filled, shows that the micropore volume of completely loaded molecular sieves has been reduced over that of the other molecular sieves.

Molecular sieves may be crystalline materials having a particle size in the range of 0.5 to 100 $\mu$m and having a uniform pore structure and micro- and/or mesopores, such as zeolites and phosphates of zeolite structure. The molecular sieves are preferably used in the form of powders. Depending on the purpose of application, however, it is also possible to use compact structures such as granulate, cylinders or the like.

Zeolites are commonly known and are described in detail, inter alia, in Chemie in unserer Zeit, 1986,4, p. 117–127 and in Angew. Chem. 1975, 18, p. 659–667. The zeolites are usually used in the acid H-form or in the neutral alkali metal form. Elements other than aluminium, including elements such as B, Ga, Fe, Cr, V, As, Sb, Bi or Be or their combinations, may be inserted into the zeolite latices. Silicon may be partially replaced with another tetravalent element, for example Ge, Ti, Zr or Hf.

If the zeolites, owing to their preparation, are not obtained in the acid H-form, but e.g. in the alkali metal or alkaline earth metal form, then the desired H-form can be generated completely or partially by ion exchange with, for example, ammonium ions and subsequent calcination or by treatment with acids.

Preferred zeolites are the zeolites A, X, Y, L, ZSM-5, ZSM-11, zeolites of the mordenite group, in particular mordenite, and faujasite type zeolites. Particularly preferred zeolites are zeolite HY, zeolite NaY, zeolite H-mordenite and zeolite LZY-52 (of Union Carbide).

It is also possible to use mesoporous silicates or metal silicates of MCM-41 structure as molecular sieve. Examples to be mentioned are: amorphous mesoporous MCM-41 having an adjustable pore width in the range of typically 3 to 10 nm (see, for example, J.of Am.Chem. Soc. 114 (1992)10834–10843, U.S. Pat. No. 5,098,684, U.S. Pat. No. 5,105,051, U.S. Pat. No. 5,134,242, U.S. Pat. No. 5,134, 243), molecular sieves of the M41S family, such as MCM-41 of hexagonal structure, MCM-50 of laminar structure (see Stud.Surf.Sci.Catal. 84 (1994) 53–60), MCM-48 of cubic structure (see Stud.Surf.Sci.Catal. 84 (1994) 53–60), FSM-16 (see Stud.Surf.Sci.Catal. 84 (1994) 125–132), metal silicates having different metals M (see WO 91/11390 for M=Al, J.Chem.Soc., Chem. Commun. (1994) 147–148 for M=Ti, J.Chem.Soc., Chem.Commun. (1994) 1059–1060 for M=V, and Prep.6th Int.Symp.Sci. Bases Heterog.Cat.1 (1994) 345–352 for M=W, Mo, Pb and Fe).

It is also known that it is possible to achieve a much higher Si/Al ratio by repeated treatment with water vapour and acid than by simple treatment with water or acid. Zeolites treated in this manner (faujasites) have a mesoporous system, i.e. they have pores having a diameter in the range from 2 to 50 nm (20 to 500 Angstrom). The entire volume of this mesoporous system is mainly influenced by the original number of Al atoms in the zeolite framework. In this case, the mesopores produced in this manner are usually bound to the external surface of the zeolite (Inorg.Chem. 15(2) (1976) 295–297; J.Phys.Chem. 93 (1989) 3677–3683; Zeolites 14 (1994) 533–540; Microporous Materials 6 (1996) 311–320).

The porous structure of molecular sieves, in particular of zeolites, may be characterised by nitrogen adsorption. The volume of the microporous system (pore diameter less than 2 nm (20 Angström)) is usually determined by means of the so-called t-plot equation. The specific surface of micro- and mesoporous solids is determined by the BET method. The mesoporous structure may be characterised by means of the so-called BJH model (see e.g. J.Am.Chem.Soc. 73 (1951) 373–380).

Phosphates of zeolite structure—so-called AlPOs, SAPOs, ELSAPOs, ELAPOs, MeAPOs and ZYTs—are described in detail, inter alia, in "Alumophosphate moleculare sieves and the periodic table" Pure & Appl. Chem. Vol 58, No.10, p.1351 to 1358 (1986), and in U.S. Pat. No. 4,310,440 (AlPO), EP-A-103,117, U.S. Pat. No. 4,440,871 (SAPO) and J 59/217,619 (ZYT).

To be mentioned as examples are AlPO-5, AlPO-8, AlPO-9, AlPO-11, AlPO-12, AlPO-14, AlPO-21, AlPO-25, AlPO-31, AlPO-33 and MCM-9. Syntheses of these compounds are described in EP-A 132 708, U.S. Pat. No. 4,310,440 and J.Am.Chem.Soc. 104 (1982) 1146. Compounds which may be used as SAPO are SAPO-5, SAPO-8, SAPO-11, SAPO-31 and SAPO-34. The preparation of these compounds is described in detail in EP-A 103,117 and U.S. Pat. No. 4,440,871. Typical examples of other silicon aluminium phosphates which may be used are ZYT-5, ZYT-6, ZYT-7, ZYT-9 and ZYT-12 (see J 59 217 619).

It is also possible to use molecular sieves of VPI-5 structure (M. E. Davis et al. J.Phys.Chem. 1991, 95 p. 1380–1383), cloverite (gallium phosphate; Nature 352 (1991) p. 320–322) and JDF-20 (J. Chem. Soc. Chem. Commun. (1992) p. 875–876). In a preferred embodiment of this invention, the pore size of the molecular sieves is chosen from the range of 0.4 to 1.4 nm (4 to 14 Å), preferably of 0.5 to 1.2 nm (5 to 12 Å), more preferably of 0.5 to 0.8 nm (5 to 8 Å). However, as described above, it is also possible to use mesoporous zeolites having a pore size in the range of 2 to 50 nm. The colorant may be soluble (dye) as well as insoluble (pigment) compounds.

For practical reasons it is preferred to use compounds which may be sublimated so that the molecular sieve can be loaded with the colorant in the vapour phase.

Examples to be mentioned are azo pigments, for example monoazo, diazo, naphthalene, benzimidazole, diazo condensate, metal complex, isoindolinone and isoindoline pigments, indigo, quinophthalone pigments, dioxazine pigments and polycyclic pigments, such as quinacridone, phthalocyanine, perylene, perinone and thioindigo pigments and also anthraquinone pigments, such as aminoanthraquinone, hydroxyanthraquinone, anthrapyrimidine, indanthrone, flavanthrone, pyranthrone, anthanthrone and isoviolanthrone pigments and diketopyrrolopyrrole (DPP) pigments.

Preferred colorants are anthraquinone, DPP, azo and indigo pigments, typically 1,4-diketo-3,6-diarylpyrrolo-[3,4-c]pyrroles, particularly preferably the soluble N,N'-dimethyl-1,4-diketo-3,6-diarylpyrrolo-[3,4-c]pyrroles, such as N,N'-dimethyl-1,4-diketo-3,6-diphenylpyrrolo-[3,4-c] pyrrole.

In a preferred embodiment of this invention, soluble compounds are used which are obtained by chemical modification of pigments in per se conventional manner, e.g. by the introduction of customary polar functional groups such as sulfonic acid groups or ammonium groups.

The mentioned colorants are commonly known and some of them are commercially available and/or may be prepared in analogy to known processes.

The load of the molecular sieve with the colorant can normally be controlled by suitable choice of the molecular sieve and/or by the choice of the ratio of colorant to molecular sieve.

The amount of load is influenced, for example, by the type and amount of the alkali metal ions in a molecular sieve. The insertion of N,N'-dimethyl-1,4-diketo-3,6-diphenylpyrrolo-[3,4-c]-pyrrole into zeolite LiX-90, for example, succeeds to at most 13% by weight, into zeolite NaX-100 to at most 12% by weight, into zeolite KX-100 to at most 7% by weight, based on the weight of the corresponding zeolite. Accordingly, zeolite LiY-65 can be loaded with the cited colorant to at most 13% by weight, zeolite NaY-1 00 to at most 12% by weight and zeolite KY-100 to at most 3% by weight, based on the weight of the corresponding zeolite.

Maximum loading of zeolite NaY-100 (12% by weight) can also be carried out, for example, using a ratio of the cited colorant N,N'-dimethyl-1,4-diketo-3,6-diphenyl-2,5-dihydropyrrolo-[3,4-c]pyrrole to zeolite NaY-100 of 1:3, whereas loading using a ratio of e.g. 1:30 gives a maximum load of 3% by weight.

The ratio of colorant to molecular sieve is usually chosen from the range of 0.01 to 60, preferably of 0.5 to 40, particularly preferably of 0.5 to 35% by weight, based on the weight of the (unloaded) molecular sieve.

The novel molecular sieves are advantageously suitable for many purposes, such as for coloring high molecular weight organic materials such as biopolymers, plastic materials, including fibres, glasses, ceramic products, for formulations of decorative cosmetics, for the preparation of inks, printing inks, paint systems, preferably automotive lacquers, and dispersion paints.

Illustrative examples of suitable high molecular weight organic materials which can be colored with the novel compounds are vinyl polymers, such as polystyrene, poly-α-methylstyrene, poly-p-methylstyrene, poly-p-hydroxystyrene, poly-p-hydroxyphenylstyrene, polymethyl methacrylate and polyacrylamide as well as the corresponding methacrylic compounds, polymethylmaleate, polyacrylonitrile, polymethacrylonitrile, polyvinyl chloride, polyvinyl fluoride, polyvinylidene chloride, polyvinylidene fluoride, polyvinyl acetate, polymethyl vinyl ether and polybutyl vinyl ether; polymers derived from maleinimide and/or maleic anhydride, such as copolymers of maleic anhydride with styrene; polyvinyl pyrrolidone; ABS; ASA; polyamides; polyimides; polyamidimides; polysulfones; polyether sulfones; polyphenylene oxides; polyurethanes; polyureas; polycarbonates; polyarylenes; polyarylenesulfides; polyepoxides; polyolefins, such as polyethylene and polypropylene; polyalkadienes; biopolymers and their derivatives, such as cellulose, cellulose ethers and cellulose esters, such as ethylcellulose, nitrocellulose, cellulose acetate and cellulose butyrate, starch, chitin, chitosan, gelatine, zein; natural resins; synthetic resins, for example alkyd resins, acrylic resins, phenolic resins, epoxy resins, aminoformaldehyde resins, such as urea/formaldehyde and melamine/formaldehyde resins; rubber; casein; silicone and silicone resins; caoutchouc, chlorinated rubber; and also polymers which are used, for example, as binders in paints, such as novolaks derived from $C_1$–$C_6$ aldehydes, e.g. formaldehyde and acetaldehyde, and from a binuclear or mononuclear, preferably mononuclear, phenol which, if desired, may be substituted by one or two $C_1$–$C_9$ alkyl groups, one or two halogen atoms or a phenyl ring, such as o-, m- or p-cresol, xylene, p-tert-butylphenol, o-, m- or p-nonylphenol, p-chlorophenol or p-phenylphenol, or from a compound containing more than one phenolic group, typically resorcinol, bis(4-hydroxyphenyl)methane or 2,2-bis(4-hydroxyphenyl)propane; as well as suitable mixtures of the cited materials.

Particularly preferred high molecular weight organic materials, especially for the preparation of a paint system, printing ink or ink, are, for example, cellulose ethers and esters, such as ethylcellulose, nitrocellulose, cellulose acetate and cellulose butyrate, natural resins or synthetic resins (polymerisation or condensation resins), for example aminoplasts, in particular urea/formaldehyde resins and melamine/formaldehyde resins, alkyd resins, phenolic plastics, polycarbonates, polyolefins, polystyrene, polyvinyl chloride, polyamides, polyurethanes, polyesters, ABS, ASA, polyphenylene oxide, rubber, casein, silicone and silicone resins as well as their possible mixture with each other.

It is also possible to use high molecular weight organic materials in dissolved form as film formers, for example boiled linseed oil, nitrocellulose, alkyd resins, phenolic resins, melamine/formaldehyde and urea/formaldehyde resins and acrylic resins.

The cited high molecular weight organic compounds can be obtained singly or in mixtures, for example as granulate, plastics, melts or in the form of solutions, in particular for the preparation of spinning solutions, paint systems, coatings, inks or printing inks. In a particularly preferred embodiment of this invention, the novel molecular sieves are used for mass coloring polyvinyl chloride, polyamides and, in particular, polyolefins such as polyethylene and polypropylene, and for the preparation of paint systems, in particular automotive lacquers, and of powder coatings, inks, printing inks and coating compounds.

Preferred binders for paint systems to be mentioned as examples are alkyd/melamine surface coating resins, acryl/melamine surface coating resins, cellulose acetate/cellulose butyrate paints and two-component paints based on polyisocyanate of crosslinkable acrylic resins.

According to findings so far, the novel molecular sieves can be added to the material to be colored in any desired amount depending on the end use requirements. In the case of high molecular weight organic materials, for example, the novel molecular sieves can be used in amounts in the range from 0.2 to 40, preferably from 0.5 to 20% by weight, based on the total weight of the pigmented high molecular weight organic material.

The high molecular weight organic materials are normally colored with the novel molecular sieves such that said molecular sieves, if desired in the form of masterbatches, are admixed to the high molecular weight organic materials using customary suitable appliances, for example roll mills, mixing or grinding apparatus. The pigmented material is then usually brought into the desired final form by methods known per se, such as calendering, moulding, extruding, coating, casting or injection moulding.

To produce non-brittle mouldings or to reduce their brittleness, so-called plasticisers may be added to the high molecular weight substances prior to moulding. These plasticisers may be, for example: the esters of phosphoric acid, phthalic acid and sebacic acid. The plasticisers can be added before, during or after coloring the high molecular substances with the novel molecular sieves.

To obtain different shades, the novel molecular sieves can be advantageously added in admixture with fillers, transparent or opaque white, colored or black pigments and conventional luster pigments in the desired amount.

To prepare paint systems, coating compositions, inks and printing inks, the corresponding high molecular weight organic substances, such as binders, synthetic resin dispersions and the like, and the novel molecular sieves, are usually dispersed or dissolved, if desired together with customary additives, such as fillers, paint auxiliaries, siccatives, plasticisers and/or additional pigments, in a shared solvent or solvent mixture. This may be effected by dispersing or dissolving the individual components by themselves or also several together and only then bringing all components together, or by adding all of them in one go.

For printing applications, all conventional industrial printing methods may be used, such as screen printing, rotogravure, bronze printing, flexographic printing and offset printing.

Accordingly, another aspect of this invention also relates to materials such as high molecular weight organic materials, preferably biopolymers and plastic materials, ceramic products, for formulations of decorative cosmetics, paint systems, preferably automotive lacquers, printing inks, inks, dispersion paints and color filters which contain the novel molecular sieves.

As compared to colorant-containing molecular sieves of the state of the art, the novel molecular sieves have enhanced leaching and bleeding behaviour, improved thermal stability, enhanced resistance to solvents and enhanced light stability. In addition, the novel molecular sieves have better chemical resistance. Furthermore, the colorant load is higher than in comparable known compounds.

EXAMPLES

The following Examples always use molecular sieves which have been dehydrated by heating.

The molecular sieves are in this case heated to 450° C. at a heating rate of 1° C./min and are then dehydrated at this temperature and at a reduced pressure of 100 mPa ($10^{-3}$ mbar) for 12 h.

Example 1

(a) 3.03 g of zeolite HY (obtained by ion exchange from zeolite NaY, of Degussa AG) are heated with 1.01 g of quinizarin at 160° C. for three days at a reduced pressure of 300 mPa. The cooled reaction mixture is then extracted with 300 ml of pyridine at reflux in a Soxhlet apparatus until the extract in the siphon tube of the apparatus is colorless. Subsequently, the molecular sieve extracted with pyridine is extracted with 300 ml of acetone at reflux in a Soxhlet apparatus until the extact in the siphon tube is colorless. The solvent is then removed from the extracted molecular sieve at a reduced pressure of 300 mPa and at 100° C. over 12 h.

b) A stream of nitrogen is passed through a vessel filled with silicon tetrachloride at room temperature and is saturated thereby. The $SiCl_4$-saturated stream of nitrogen is then passed for 3 h over 2 g of the colorant-loaded molecular sieve prepared according to (a), which is in a tube furnace and which is heated to 150° C. Excess silicon tetrachloride is then removed by flushing for 1 hour with a pure stream of nitrogen at room temperature.

Example 2

(a) 3.00 g of an ultrastable dealuminised zeolite HY (of PQ Corporation) are heated with 1.00 g of indigo at 240° C. for three days at a pressure of 300 mPa. The cooled reaction mixture is then extracted with 300 ml of pyridine at reflux in a Soxhlet apparatus until the extract in the siphon tube is colorless. The molecular sieve extracted with pyridine is then extracted with 300 ml of acetone at reflux in a Soxhlet apparatus until the extract in the siphon tube is colorless. Subsequently, the solvent is removed from the extracted molecular sieve at a reduced pressure of 300 mPa and at 100° C. over 12 h.

b) A stream of nitrogen is passed through a vessel filled with silicon tetrachloride at room temperature and is saturated thereby. The $SiCl_4$-saturated stream of nitrogen is then passed for 3 h over 2 g of the colorant-loaded molecular sieve prepared according to (a), which is in a tube furnace and which is heated to 150° C. Excess silicon tetrachloride is then removed by flushing for 1 hour with a pure stream of nitrogen at room temperature.

Example 3

(a) 3.00 g of zeolite H-mordenite (of CU Chemie Uetikon AG) are heated with 1.01 g of indigo at 240° C. for three days at a pressure of 300 mPa. The cooled reaction mixture is then extracted with 300 ml of pyridine at reflux in a Soxhlet apparatus until the extract in the siphon tube is colorless. The molecular sieve extracted with pyridine is then extracted with 300 ml of acetone at reflux in a Soxhlet apparatus until the extract in the siphon tube is colorless. Subsequently, the solvent is removed from the extracted molecular sieve at a reduced pressure of 300 mPa and at 100° C. over 12 h.

b) A stream of nitrogen is passed through a vessel filled with silicon tetrachloride at room temperature and is saturated thereby. The $SiCl_4$-saturated stream of nitrogen is then passed for 3 h over 2 g of the colorant-loaded molecular sieve prepared according to (a), which is in a tube furnace and which is heated to 150° C. Excess silicon tetrachloride is then removed by flushing for 1 hour with a pure stream of nitrogen at room temperature.

Example 4

Example 3 is repeated, but using as colorant 0.84 g of N,N'-dimethyl-1,4-dike-to-3,6-diphenylpyrrolo-[3,4-c] pyrrole (prepared according to Example 1 of U.S. Pat. No. 4,585,878; hereinafter called DPP1) and 3.01 g of zeolite NaY (of Degussa AG). The solvent is then removed over 12 h and the zeolite is loaded with DPP1 at 150° C.

Example 5

The procedure of Example 4 is repeated, but replacing zeolite NaY with 7.01 g of zeolite H-mordenite (of CU Chemie Uetikon AG) and 2.33 g of DPP1.

Example 6

To test the behaviour of the modified colorant-loaded molecular sieve with respect to leaching, 0.2 g each of the molecular sieves prepared according to Examples 1 to 5 of this invention are coated with 2 ml each of N-methylpyrrolidone (NMP), acetone and pyridine as solvent (see Table below). The samples prepared in this manner are left standing at room temperature for six months. After this time, no coloration is found in the solvents of the samples. The results obtained are compiled in the following Tables.

TABLE

Overview over the leaching behaviour of the modified colourant-loaded molecular sieves

| Example | Colourant | Zeolite | Coloration in acetone | pyridine | NMP |
|---|---|---|---|---|---|
| 1 | quinizarin | HY | — | — | — |
| 2 | indigo | HY | — | — | — |
| 3 | indigo | H-mordenite | — | — | — |
| 4 | N,N-dimethyl-DPP | NaY | — | — | — |
| 5 | N,N-dimethyl-DPP | H-mordenite | — | — | — |

Example 7

(a) The thermal stability of a molecular sieve prepared in Example 4 is tested in air at a heating rate of 2 K/min by DSC. Aluminium oxide is used as reference. The loss in mass is completed at 573° C. (b) The test is carried out using a molecular sieve prepared in general annalogy to the one of Example 4 without, however, any modification with silicon tetrachloride. In the case of this unmodified molecular sieve the loss in mass is already completed at 526° C.

Example 8

0.2 g of the pigment prepared in Example 3 is mixed with 13.3 g of polyvinyl chloride (Evipol®SH 7020, of EVC GmbH) and 7.3 ml of a stabiliser mixture consisting of 92.21% by weight of DIDP Vestinol®, of Hüls Chemie, 4.19% by weight of Rheoplast®39, Ciba-Geigy, and 3.6% by weight of IRGASTAB®BZ561, of Ciba-Geigy, and this mixture is then processed to a thin film on a roll mill for 15 minutes at 160° C. The colored film so obtained is resistant to migration, i.e. no bleeding of the novel molecular sieve on an uncolored film is found.

What is claimed is:

1. A molecular sieve, which contains colorant molecules in at least some of its cavities as well as a modifier which is covalently bound to said molecular sieve and which reduces its pore diameter.

2. A molecular sieve according to claim 1, which is obtained either (a) by completely or partially filling its cavities with colorant molecules and subsequent reaction with a modifier, or (b) by reducing the pore diameter of a molecular sieve, which already has at least some of its cavities filled with colorant molecules, by reaction with a modifier.

3. A molecular sieve according to claim 1, wherein the modifier is at least one compound selected from the group consisting of metal halides, silicone alkoxides, carbon/tin compounds, silicon hydride compounds, tetraalkylorthosilicates, monoalkyl-, dialkyl-, trialkyl- and triarylchlorosilanes, disiloxanes, diborane, silicate sols, silicate colloids and halogenated polysiloxanes.

4. A process for the preparation of a molecular sieve according to claim 1, which comprises (a) completely or partially filling the cavities of a molecular sieve with colorant molecules and subsequently reducing its pore diameter by reaction with a modifier, or (b) reducing the pore diameter of a molecular sieve, which already has at least some of its cavities filled with colorant molecules, by reaction with a modifier.

5. A method of coloring a high molecular weight organic or inorganic material which comprises adding a tinctorially effective amount of a molecular sieve according to claim 1 thereto as pigment.

6. A method according to claim 5 wherein the high molecular weight organic material is a biopolymer or a plastic material.

7. A method according to claim 5 wherein the molecular sieve is added as a colorant to formulate decorative cosmetics or paint systems.

8. A method according to claim 5 wherein the paint system is an automotive lacquer, a printing ink, an ink or a dispersion paint.

9. A method according to claim 5 wherein the high molecular weight inorganic material is a glass or a ceramic product.

10. A method according to claim 5 wherein the organic or inorganic material is a color filter.

* * * * *